United States Patent
Zhai (10) Patent No.: US 10,182,790 B2
(45) Date of Patent: Jan. 22, 2019

(54) ADAPTIVE TIMING GUIDANCE IN STRESS ECHOCARDIOGRAPHY

(71) Applicant: Siemens Medical Solutions USA, Inc., Malvern, PA (US)

(72) Inventor: Liang Zhai, Castro Valley, CA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 693 days.

(21) Appl. No.: 14/673,274

(22) Filed: Mar. 30, 2015

(65) Prior Publication Data

US 2016/0287208 A1 Oct. 6, 2016

(51) Int. Cl.
| | |
|---|---|
| *A61B 8/00* | (2006.01) |
| *A61B 8/02* | (2006.01) |
| *A61B 8/08* | (2006.01) |
| *A61B 5/00* | (2006.01) |
| *A61B 5/0245* | (2006.01) |
| *A61B 5/0456* | (2006.01) |

(52) U.S. Cl.
CPC .............. *A61B 8/02* (2013.01); *A61B 5/0245* (2013.01); *A61B 5/4884* (2013.01); *A61B 8/0883* (2013.01); *A61B 8/5223* (2013.01); *A61B 5/0456* (2013.01)

(58) Field of Classification Search
CPC ....... A61B 8/02; A61B 5/0245; A61B 8/0883; A61B 8/5223; A61B 5/4884; A61B 5/0456
USPC ................................. 600/437–469
See application file for complete search history.

(56) References Cited

U.S. PATENT DOCUMENTS

| | | | | |
|---|---|---|---|---|
| 4,898,182 | A | * 2/1990 | Hawkins | A61B 5/222 600/509 |
| 6,540,676 | B2 | 4/2003 | Kamiyama | |
| 7,463,919 | B2 | * 12/2008 | Hamilton | A61B 5/055 600/410 |
| 8,715,182 | B2 | 5/2014 | Ogasawara | |
| 2003/0114275 | A1 | 6/2003 | Falbo et al. | |
| 2003/0163045 | A1 | * 8/2003 | Gatzke | A61B 5/00 600/437 |
| 2004/0077952 | A1 | * 4/2004 | Rafter | A61B 6/563 600/481 |
| 2004/0243190 | A1 | * 12/2004 | Ben-Haim | A61B 5/0215 607/9 |

(Continued)

FOREIGN PATENT DOCUMENTS

| | | |
|---|---|---|
| CN | 101081172 A | 12/2007 |
| CN | 101152096 A | 4/2008 |

(Continued)

OTHER PUBLICATIONS

S.N. Berberish, et al., "A Practical Approach to Exercise Echocardiography: Immediate Postexercise Echocardiography," JACC, vol. 3, No. 2, Feb. 1984, pp. 284-290.

(Continued)

*Primary Examiner* — Sanjay Cattungal (57) ABSTRACT

Guidance is provided in stress echocardiography. The recovery time after cessation of the stress is predicted using patient-specific information. The prediction may assist the user in acquiring images of the heart for stress echocardiography during the patient-relevant period, avoid unnecessary rush, and/or avoid acquisition of less useful images.

20 Claims, 3 Drawing Sheets

(56) References Cited

U.S. PATENT DOCUMENTS

| | | | | |
|---|---|---|---|---|
| 2006/0032315 | A1* | 2/2006 | Saalastic | A61B 5/222 73/808 |
| 2008/0140142 | A1* | 6/2008 | Darvish | A61N 1/05 607/11 |
| 2008/0285819 | A1* | 11/2008 | Konofagou | A61B 8/08 382/128 |
| 2009/0161938 | A1* | 6/2009 | Shekhar | A61B 8/0883 382/131 |
| 2009/0259121 | A1* | 10/2009 | Simonetti | A61B 5/0046 600/410 |
| 2011/0208016 | A1* | 8/2011 | Bombardini | A61B 5/021 600/301 |
| 2013/0096639 | A1* | 4/2013 | Ben-Haim | A61N 1/14 607/11 |
| 2013/0165781 | A1* | 6/2013 | Cardinale | A61B 5/044 600/440 |
| 2014/0128735 | A1 | 5/2014 | Newell et al. | |
| 2016/0113631 | A1 | 4/2016 | Chono et al. | |
| 2016/0287208 | A1* | 10/2016 | Zhai | A61B 8/02 |
| 2017/0189265 | A1* | 7/2017 | Freeman | A61H 31/005 |

FOREIGN PATENT DOCUMENTS

| | | |
|---|---|---|
| CN | 101461722 A | 6/2009 |
| CN | 103153196 A | 6/2013 |
| JP | H06285066 | 10/1994 |
| JP | H11128227 | 5/1999 |
| JP | 2004283518 | 10/2004 |

OTHER PUBLICATIONS

R. Sicari, et al., "Stress echocardiography expert consensus statement," European Journal of Echocardiography (2008), 9, pp. 415-437.

P.A. Pellikka, et al., "American Society of Echocardiography Recommendations for Performance, Interpretation, and Application of Stress Echocardiography," Journal of the American Society of Echocardiography, vol. 20, No. 9, 2007, pp. 1021-1041.

A. Franke, "The stress echo dilemma: time counts, but image quality too," European Heart Journal (2006) 27, pp. 1646-1647.

T.C. Andrews, et al., "Subsets of Ambulatory Myocardial Ischemia Based on Heart Rate Activity—Circadian Distribution and Response to Anti-Ischemic Medication," The Angina and Silent Ischemia Study Group (ASIS), 1993, vol. 88, No. 1, pp. 92-100.

L. Wang, et al., "Time constant of heart rate recovery after low level exercise as a useful measure of cardiovascular fitness," Proceedings of the 28th IEEE, EMBS Annual International Conference, 2006, pp. 1799-1802.

M. Javorka, et al., "Heart rate recovery after exercise: relations to heart rate variability and complexity," Brazilian Journal of Medical and Biological Research, (2002) 35:, pp. 991-1000.

Office Action for corresponding application No. 201610440590.9 dated May 28, 2018.

* cited by examiner

ADAPTIVE TIMING GUIDANCE IN STRESS ECHOCARDIOGRAPHY

BACKGROUND

The present embodiments relate to medical ultrasound imaging. In particular, stress echocardiography is performed within a limited time window after ending the stress on the patient.

Stress echocardiography evaluates cardiac function by studying the cardiac wall motion and thickness in response to stress caused by physical exercise or medical agents. During exercise echocardiography, the patient exercises on a treadmill or a bicycle machine until their heart rate reaches a targeted level. Imaging during exercise (e.g., on a treadmill) may not be feasible. Because exercise induced abnormal wall motion only lasts for a short amount of time, images have to be acquired immediately after the cessation of exercise. The duration of exercise-induced abnormal wall motion is patient dependent and generally less than three minutes after the cessation of exercise. The American Society of Echocardiography recommends image acquisition within one to two minutes after the cessation of exercise, while the European Association of Echocardiography recommends less than one minute.

In practice, the protocol varies from one health provider to another, with the duration of post stress imaging arbitrarily set from one to ten minutes post-stress image acquisition. When a protocol uses a very short duration, for example within 1 minute after the cessation of exercise, obtaining quality data is challenging. When a protocol uses a longer duration, a large amount of data may be useless or less useful. Images acquired after the heart rate has dropped low enough show no or little abnormal wall motion.

BRIEF SUMMARY

By way of introduction, the preferred embodiments described below include methods, systems, and computer readable media for stress echocardiography guidance. The recovery time after cessation of the stress is predicted using patient-specific information. The prediction may assist the user in acquiring images of the heart for stress echocardiography during the patient-relevant period, avoid unnecessary rush, and/or avoid acquisition of less useful images.

In a first aspect, a method is provided for stress echocardiography guidance. A plurality of heart rate intervals of a patient are detected from an EKG device. An ultrasound imaging system calculates a rate of recovery for the patient from the heart rate intervals and estimates a time for imaging a heart of the patient while recovering from stress. The time is estimated as a function of the rate of recovery. The time is output on a display of the ultrasound imaging system.

In a second aspect, a non-transitory computer readable storage medium has stored therein data representing instructions executable by a programmed processor for stress echocardiography guidance. The storage medium includes instructions for computing a time for image acquisition during stress echocardiography of a patient with an ultrasound scanner, adapting the computing as a function of an electrocardiography signal for the patient and from an electrocardiography sensor, and outputting an indication of the time.

In a third aspect, a system is provided for stress echocardiography guidance. An ultrasound scanner is configured for performing stress echocardiography of a patient. An input of the ultrasound scanner is connectable with an electrocardiography device. A processor is configured to calculate a post-stress time window for the stress echocardiography of the patient. The processor calculates the post-stress time window as a function of electrocardiography information received at the input.

The following claims define the present invention, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Adaptive timing guidance is provided for stress echocardiography. The timing control is personalized to individual patients. The duration of post-stress abnormal wall motion may be different depending on individual patients. Rather than operating on a generalized protocol, the valid time window of imaging for individual patients is predicted. Providing this predication as guidance to a sonographer may help obtain valuable data and improve diagnostic accuracy of stress echocardiography.

The post-stress imaging time window is calculated based on electrocardiography (ECG) data of an individual patient. The time window for image acquisition is adaptively computed based the patient-specific ECG data. During imaging, the time window prediction may be updated in real-time. The time may be visually or audibly indicated to guide image acquisition. The timing information indicates the usefulness of acquired data during acquisition or post acquisition review and intuitively guides the imaging.

Figure 1:
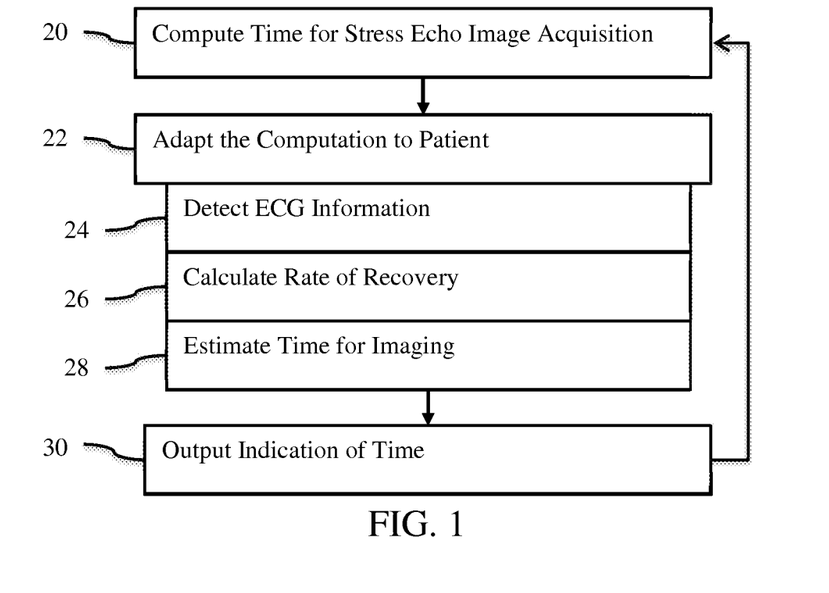
FIG. 1 is a flow chart of one embodiment of a method for stress echocardiography guidance.

FIG. 1 shows a method for stress echocardiography guidance. The sonographer is assisted in performing stress echocardiography. Timing information is presented to the user for determining a remaining time to collect useful data (e.g., remaining time during which the heart rate has not yet recovered from stress) or for another purpose. The timing information is patient specific, such as adapting to a given patient. The timing information may adapt in real-time in an ongoing manner, once, and/or while the heart rate of the patient is recovering.

Figure 5:
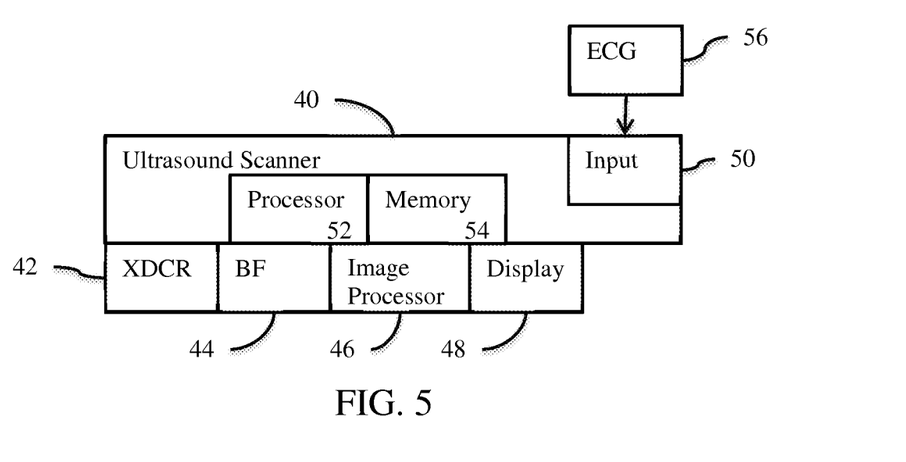
FIG. 5 is a block diagram of one embodiment of a system for stress echocardiography guidance.

The method is performed by the system of FIG. 5, an ultrasound scanner, a processor, or different systems or device. In one embodiment, an ultrasound imaging system also being used to perform the stress echocardiography performs all of the acts of FIG. 1. In other embodiments, a processor of an ECG device performs act 24 and/or other acts (e.g., 20, 22, 26, 28, and/or 30).

Additional, different or fewer acts may be performed. For example, acts 24-28 provide one example for adapting, but other acts may be used to adapt the timing computation of act 20 to the patient. Act 28 is one instance of performance of act 20, but may be a separate estimation. As another example, acts for performing the stress echocardiography are provided. In yet another example, the indication of the time is recorded or stored rather than or in addition to being output.

The acts are performed in the order shown or a different order. The acts are performed from top to bottom of FIG. 1. Alternatively, the adaptation of act 22 occurs before the computation of the time in act 20.

The acts are performed prior to and/or during stress echocardiography. In stress echocardiography, an ultrasound scanner acquires B-mode images of a patient's heart. Color flow and/or spectral Doppler images may be acquired. A processor may determine wall thickness or perform another stress echocardiography measurement. To acquire images or measure, ultrasound energy is used to scan a one, two, or three-dimensional field of view of the patient. The field of view includes at least a portion of the heart of the patient. One or more images are generated from the scan. Any now known or later developed modes of imaging may be used.

In act 20, a time for image acquisition is computed. The time is for acquisition of images during stress echocardiography. The time may be calculated prior to or during the stress echocardiography, but relates to when to acquire images. The time indicates a remaining time for acquiring images before less effective imaging results from recovery or sufficient recovery of the heart rate. The ultrasound scanner is to acquire images within a desired time window during recovery of the heart of the patient after cessation of stress. The time is for acquisition of the images during the recovery.

In one embodiment, the time is a remaining time or amount of time left to scan. In other embodiments, the time is an absolute time, such as a clock time at which less effective imaging results and/or recovery of the patient's heart rate is sufficient to make imaging less useful in stress echocardiography. In other approaches, the time is a difference from an end point or from when imaging is predicted to be less effective. The time may be a positive or negative value. For example, images acquired after the recovery time are labeled with negative times. Images acquired before the recovery time are labeled with positive times.

The time is computed as a function of a heart rate of the patient. Due to stress, the patient's heart rate is more rapid than normal. After the stress ceases, the heart rate begins to recover. The heart rate becomes less over time, eventually reaching a steady state. Since the goal of stress echocardiography is to measure the effects of the stress, the imaging is to be performed prior to recovery. Imaging just before recovery may not be as effective as imaging closer in time to the cessation.

The length of a heart cycle is an inverse of the heart rate. Where heart rate is used herein, the interval may instead be used. Similarly, where the interval is used, the heart rate may be used instead.

Any of various variables may be used in calculating the time for stress echocardiography imaging. In one embodiment, the heart rate or interval and a time constant are used. In other embodiments, weighting constants, offset constants, or other variables are used. Acts 24-28 provide one example for computing the time. Other examples using data representing recovery specific to a patient may be used, such as treating recovery as a linear relationship with time and/or using a starting steady state heart rate. The goal is to compute a time at which stress echocardiography imaging transitions from desired imaging to undesired or not sufficiently effective imaging.

In act 22, the computation of the time adapts as a function of the patient. The time is a function of patient specific information. The blood pressure, heart rate, or other information acquired from or representing a given patient is used as a variable in the computation. More than one variable may adapt to a given patient. In one embodiment, the interval of the heart cycle acquired from electrocardiography (ECG) signals for the patient is used. An ECG sensor indicates the interval or a heart cycle trace from which the interval is derived. In other embodiments, ultrasound scanning is used to measure the interval or heart rate, such as using color flow or spectral Doppler to extract the heart cycle.

Figure 2:
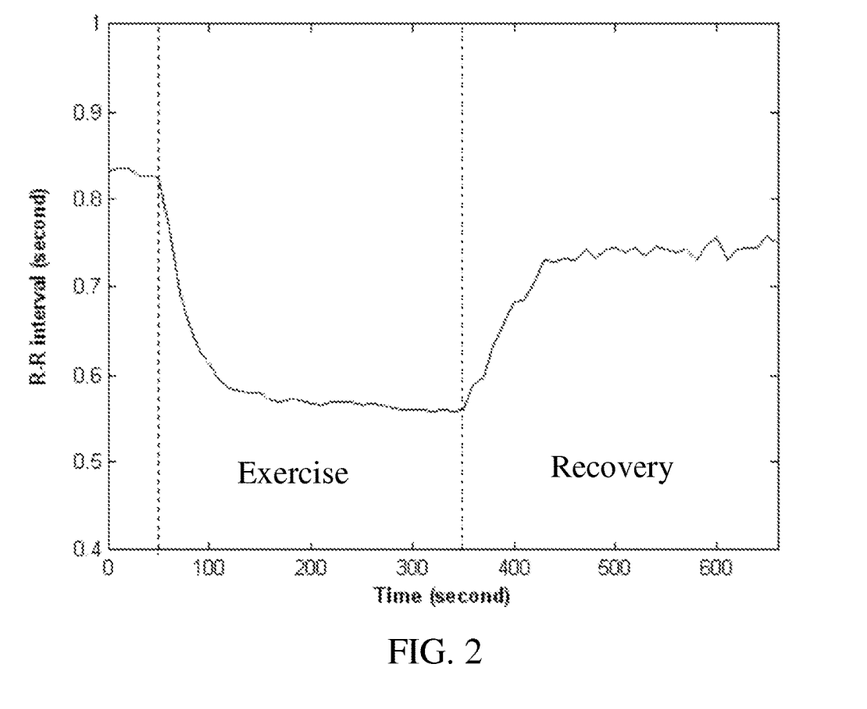
FIG. 2 is a graph showing a heart interval as a function of time during stress and recovery.

FIG. 2 shows an example graph of a heart cycle interval as a function of time. The interval is measured from R-wave repetition, so is the R-R (the time elapsing between two consecutive R waves) interval. Other phases of the heart cycle may be used to measure the interval or length of the heart cycle. Heart rate may be used instead of interval.

The interval is shown during both exercise (i.e., application of stress) and recovery after ceasing the stress. Each heart cycle of a patient without stress or in steady state may last about one second. Different patients have different steady state heart intervals. Similarly, different patients may have different intervals under a given amount of stress, rate of interval change due to stress, rate of interval change during recovery, and/or other characteristic of the interval curve.

In FIG. 2, the curve shows that the R-R interval decreases during exercise as the heart rate goes up from about 50 seconds to 350 seconds. The interval curve then increases during the recovery as the heart rate goes down after ceasing the stress at about 350 seconds. In this example, effective stress echocardiography imaging occurs between 350 seconds and 425 seconds. Other intervals or rate of change of the interval may be used for the change to less effective imaging.

The heart rate recovery process after exercise may be modeled by equation 1:

$$RR(t) = b - ae^{\left(-\frac{t}{\tau}\right)} \quad [1]$$

Equation 1 gives the interval as a function of an offset constant, b, a weight constant a, the time t, and a time constant τ. The function is an exponential. Other models may be used, such as using different, additional, or fewer variables. Any of the variables may be treated as constants that do not vary among patients. One or more of the constants may be treated as varying among patients, such as the time constant and the weight constant.

The recovery rate of the interval is a derivative of the interval. For example, the recovery rate, r, as a function of time, t, is:

$$r(t) = \frac{dRR(t)}{dt} = \frac{a}{\tau}e^{-\frac{t}{\tau}} \quad [2]$$

Solving for a given time, $T_0$, the recovery rate at that time is:

$$R_0 = r(T_0) = \frac{a}{\tau} e^{-\frac{T_0}{\tau}} \qquad [3]$$

Equations 2 or 3 may be used to determine a constant appropriate for a given patient and/or a given patient for a given stress. In one embodiment, the time constant for a patient is calculated from a change in the heart rate as a function of time from the electrocardiography signal of the patient. The time constant and/or other variable is used to adapt the computation of the time as a function of the curve of interval as a function of time specific to the patient. The curve represents the recovery of the heart rate of the patient. By fitting a curve or model to the measured heart rate or interval information for a specific patient, one or more characteristics of the curve or model for that patient may be determined and used to calculate the time.

Acts 24, 26, and 28 represent one embodiment for adapting the computation of the time. Additional, different, or fewer acts may be provided.

In act 24, a plurality of heart rate intervals of a patient are detected from an ECG device. The ECG device outputs a heart rate, so the inverse of the heart rate is used. Alternatively, the ECG device outputs a heart cycle trace. A processor of the ultrasound imaging system determines the heart interval or rate from the trace.

Any heart interval or rate calculation may be used. In one embodiment, an R-wave detector is applied. The R-wave is detected from a change in slope of the heart cycle trace that also has a sufficiently high magnitude peak. Other R-wave detection techniques may be used. Other phases of the heart cycle may be used. By detecting successive or sequential R-waves, the R-R interval (e.g., length of the heart cycle) and heart rate are measured.

Any number of intervals or heart rate measurements may be detected. For example, two or more (e.g., at least three or four) intervals are detected. The detection occurs upon cessation of the stress. A patient is connected to the ECG device during the exercise or other stress-inducing activity. Upon ceasing the stress, output from the ECG device is used to detect the heart rate intervals. For example, upon the cessation of the exercise, a few beats of ECG data (e.g. 4 beats) are acquired, and the R-R intervals are calculated from the ECG data.

In act 26, a rate of recovery is calculated. The rate of recovery specific to the patient may be calculated from the detected heart rates or heart rate intervals. The recovery rate is based on the ECG data of the patient. For example, the detected intervals are samples along the recovery curve. The time of detection of the interval and the length of the interval are measured. By plotting the interval as a function of time, samples along the recovery curve for the patient are provided.

A curve is fit to the samples to determine the recovery curve specific to the patient. An exponential, polynomial, or other curve is fit to the samples. Linear regression or other curve fitting is performed. Alternatively, a model is used. The rate of recovery is calculated from the samples without curve fitting.

Figure 3:
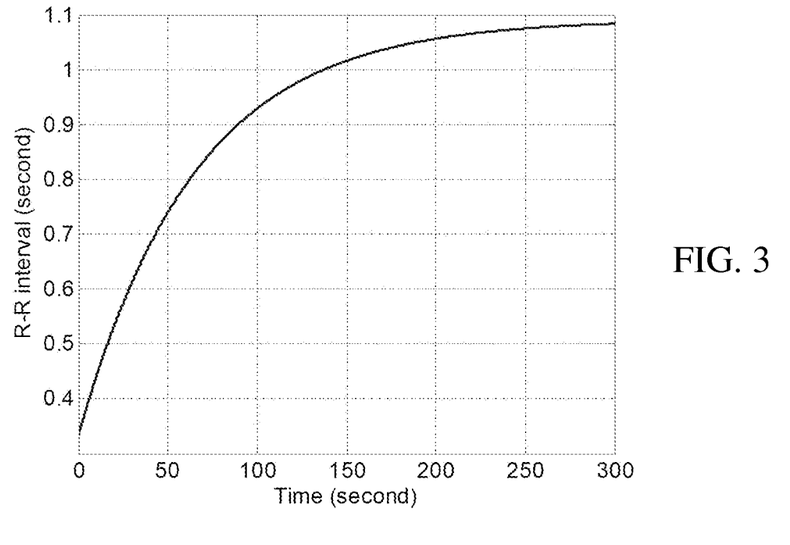
FIG. 3 is a graph showing a calculated curve of heart interval as a function of time.
Figure 4:
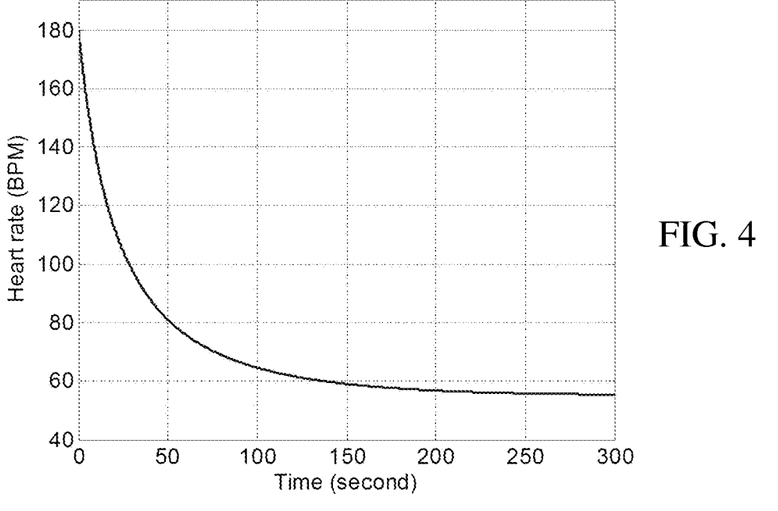
FIG. 4 is a graph showing a heart rate as a function of time.

Using the fit curve and/or samples, the constants forming the model of the recovery are calculated for the patient. FIG. 3 shows an example recovery curve resulting from the model represented by equation 1. The curve uses b=1.09 s, a=0.76 s, and $\tau$=65 s. FIG. 4 shows the corresponding simulated recovery curve of heart rate, the inverse of the curve of FIG. 3. Instead of using equation 1 as the model, equation 2 may be used as the model. A derivative or change in the detected intervals with change in time is used.

To determine the patient-specific constant, the detected samples or fit curve are used. For example, the model of equation 2 is used. "a" is treated as constant for all patients, such as a value of 0.75 s or other value. The time constant for the specific patient is calculated. Using the R-R intervals, $\tau$ is found using equation 2. Equation 1 or other model may be used. Where more than two measures of the interval are provided, the time constant may be calculated multiple times. An average, median or other statistical combination of the different time constants resulting from the measures for the patient may be used.

Natural phenomenon and/or measurement noise cause variability in the intervals. The intervals, curve fit to the intervals as a function of time, or other ECG data used to derive the intervals may be filtered. A low pass filter removes higher frequency noise to smooth the information, reducing variability of the time constant.

In other embodiments, more than one variable is calculated for the patient. For example, "a" and/or "b" are calculated for a specific patient. Any solution for the number of variables given the number of detected intervals may be used.

The constants are used to reflect the rate of recovery. Where a curve fitting is used, the curve represents the rate of recovery. Either or both of the curve fitting or constants may be used. The rate of recovery is calculated using the constants from the model, such as equation 2. Alternatively, the rate of recovery is calculated as a change in slope of the curve. In yet other embodiments, the rate of recovery is not specifically calculated. The constant or curve is calculated to represent the rate of recovery. Other characteristics of the recovery specific to a given patient may be used.

In act 28, the time for imaging of the heart of the patient is estimated. The processor estimates the time until the heart rate recovers. After ceasing the stress, the time until recovery or a threshold amount of recovery occurs is determined. The time it takes for the rate of recovery to drop to a threshold is predicted.

The time is estimated as a function of a threshold. The threshold is a predetermined value, such as set by programming. A typical or experimental value may be used. In other embodiments, a sonographer, policy of an institution, or recommendation of a medical group is used.

The threshold heart rate indicates the heart rate at which imaging is considered effective. Any threshold heart rate may be used, such as a standard rate or sonographer set rate. In other embodiments, the change in heart rate is used. When the amount of change in heart rate becomes less, then the imaging is considered less effective. The threshold is an interval, heart rate, a recovery rate, a change in recovery rate, or other characteristic of the model or recovery curve.

The threshold defines a time along the recovery curve at which imaging transitions from sufficient to insufficient. The transition may be arbitrary or set to include less accurate images or avoid inclusion of less accurate images. Any threshold may be used. The threshold is set relative to expected abnormal wall motion persistence in recovery. The threshold is selected to be at a point along the recovery curve or in the model where the rate of the heart rate recovery decreases to be less representative of abnormal wall motion, assuming abnormal wall motion occurs for the patient.

In an example using the model of equation 2, r is the change in the recovery rate over time. $R_0$ of equation 3 is set as the threshold amount of change in the recovery rate to represent the transition. The threshold change occurs at time $T_0$. The time $T_0$ is estimated.

The estimation of the time is a function of the rate of recovery or other patient-specific recovery characteristic calculated in act 26. For example, the processor calculates a change in time of a heart rate as a function of the patient-specific time constant. The time is a function of a heart rate derived from the rate of recovery. The time is estimated from change in the heart rate intervals as a function of time.

The time is estimated as a current time plus the change. Instead of or in addition to estimating an absolute time (e.g., 3:25:43), the time is estimated as a change in time or time difference from a current time (e.g., in 68 seconds).

In one embodiment, the change in time, $\Delta t$, is determined by combining equations 2 and 3, giving:

$$\Delta t = T_0 - t = \tau \ln \frac{r(t)}{R_0} \quad [4]$$

Equation 4 shows the time it takes the recovery rate to reach the threshold value from the current time t, when $\Delta t > 0$. When $\Delta t < 0$, the absolute value $|\Delta t|$ shows the time that has passed since the threshold value. Other estimates of the time may be used. For example, the threshold is applied to the recovery curve for the patient to find the absolute time.

In act 30, an indication of the time is output. The indication is an audio and/or visual indication. The audio indicator may be any audible sound, such as a click, beep, chirp, noise burst, voice recording, or combination thereof. For example, a beep or sequence of more rapid beeps are generated by a speaker to signify the time and/or approaching the time.

Visual indicators may be text or other visible output on a display. The time or remaining time is output as text on or beside ultrasound images on a display of an ultrasound imaging system. As the imaging continues, the time may count down. If imaging continues past the time, the time may count up.

For non-textual visual indication, blinking, coloring or combinations thereof of textual, graphical, or other symbols may be used. In other visual indications, a graph is displayed. The graph may be a bar that shrinks or expands to represent approaching the time. The graph may be the modeled recovery curve for the patient with a marker or color-coding to indicate the current time, the threshold time, and/or a time difference. A blinking light may be used.

The indication has predetermined or set characteristics. Alternatively, one or more characteristics are controlled as a function of the time or other recovery curve or model characteristic. The indication may vary as the time is closer, such as changing color or flashing when the time is within a threshold period.

The indicator provides a time relative to the recovery of the heart rate of the patient. The visual and/or auditory indicators may be used to guide the image acquisition during stress echocardiography. For example, $\Delta t$ is visually displayed using text or a graph on the screen and updated in real time to show the sonographer the amount time left for acquiring useful images.

Review of previously acquired stress echocardiography images may benefit from indication of the time. The time is output with an image displayed during review. The time is for when the image was acquired relative to the recovery. During reviewing, an indicator indicates where the current image was acquired before or after the threshold time.

FIG. 1 shows a feedback from act 30 to act 20. The feedback may be from act 28 and/or to another act. The feedback represents repetition of the acts during an imaging session. While the recovery is occurring, the time estimation or computation may be updated based on more recent information. Other heart rate intervals are detected. The more recently detected intervals are used instead or in addition to previously detected intervals to again compute the time. For example, r(t) is calculated for every interval measured from ECG data. The time constant, other constant, curve, or curve characteristic is re-calculated using the set of available ECG data. The change in rate or other timing relative to the recovery information is estimated using the repetition updated values and/or curves. The detecting of act 24, calculating of act 26, estimating of act 28, and outputting of act 30 are repeated with additional heart rate intervals as the recovery and imaging continue.

FIG. 5 shows one embodiment of a system for stress echocardiography guidance. During stress echocardiography, the sonographer is guided by an indication of time relative to recovery of the heart rate from stress. For review after stress echocardiography, the reliability of images is indicated, in part, by timing of the acquisition of the image relative to the recovery.

The system implements the acts of FIG. 1. For example, the processor 52 implements the acts with output of the indication of act 30 being to the display 48. As another example, the ECG device 56 implements act 24. Alternatively, the system implements different, additional, or fewer acts.

The system includes a medical diagnostic ultrasound scanner 40 and an ECG device 56. Additional, different, or fewer components may be provided. For example, a processor outside the ultrasound scanner 40 for analyzing ECG signals is provided. As another example, the ECG device 56 is integrated within the ultrasound scanner 40. In yet another example, the ECG device 56 is not provided as the ultrasound scanner 40 uses ultrasound data to determine the heart cycle characteristics (e.g., interval). For another example, a speaker is provided.

The ECG device 56 is a processor, circuit, and/or electrodes. Any now known or later developed ECG device may be used. By placing the electrodes on a patient, the heart trace of the patient's heart cycle is generated. The ECG device 56 detects the R-waves, other phases, interval, and/or heart rate of the heart cycle. Alternatively, the ultrasound scanner 40 detects the phases of the heart cycle from a trace signal received from the ECG device 56.

The ultrasound scanner 40 is a medical diagnostic ultrasound imaging system. In other embodiments, the ultrasound scanner 40 is a therapy system that may also image. Any now known or later developed system for stress echocardiography may be used. The ultrasound scanner 40, using the processor 52 as a controller, with hardware, and/or with software is configured for performing stress echocardiography of a patient. During an imaging session, the transducer probe 42 is positioned to scan the heart of the patient, and images are generated during recovery of the heart rate after cessation of stress, such as exercise.

The ultrasound scanner 40 includes a transducer probe 42, a beamformer 44, an image processor 46, a display 48, an input 50, a processor 52, and a memory 54. Additional, different or fewer components may be provided. For example, the image processor 46 and processor 52 are combined. As another example, the memory 54 is remote or not part of the ultrasound scanner 40. As yet another example, a scan converter, temporal filter, spatial filter, speaker, or other ultrasound imaging components are provided.

The transducer probe 42 has a housing and an array of transducer elements. The housing is adapted or shaped for handheld use on the exterior of the patient. Alternatively, the housing is shaped as a catheter, intraoperative probe, intercavity probe, transesophageal probe or other now known or later developed transducer probe. The array is a linear, multidimensional, annular or other now known or later developed array of piezoelectric or microelectromechanical elements.

The transducer probe 42 generates acoustic energy in response to electrical signals from the beamformer 44. For imaging, acoustic echoes received by the transducer probe 42 are transduced into electrical signals, and the transducer probe 42 provides the electrical signals to the beamformer 44.

The beamformer 44 is a transmit beamformer, receive beamformer or both transmit and receive beamformer. As a transmit beamformer, the beamformer 44 includes waveform generators or pulsers, delays, phase rotators, timing generators, amplifiers, combinations thereof or other now known or later developed transmit beamformer components in a plurality of channels. For transmission, the beamformer 44 generates relatively delayed and apodized waveforms for each of a plurality of channels for a corresponding plurality of transducer elements. The transducer probe 42 forms an acoustic beam or beams in response to the waveforms.

As a receive beamformer, the beamformer 44 includes channels with delays, phase rotators, amplifiers, or combinations thereof and includes a summer or summers for adding the signals from each channel together. For reception, the beamformer 44 generates samples representing different spatial locations. Samples for B-mode, flow mode, Doppler mode, spectral Doppler mode, harmonic imaging, contrast agent detection or other modes are generated.

The receive beamformed samples are provided to the image processor 46 for generating an image. The image processor 46 is a detector, filter, scan converter, three-dimensional processor, combinations thereof or other now known or later developed image generator. The detection is B-mode (intensity), flow-mode (velocity, energy, and/or variance), spectral Doppler and/or other detectors. The samples are detected, scan converted and provided to the display 48.

The display 48 is a monitor, liquid crystal display, plasma display, light emitting diode display, printer, projector, or other device for outputting one or more images for viewing. Any now known or later developed display device may be used. The display 48 is part of the ultrasound scanner 40, but may be a remote device, such as a wall mounted or remote workstation display.

The display 48 shows one or more images of the patient's heart. The images are generated as part of stress echocardiography. During the stress echocardiography, the ultrasound scanner 40 also outputs guidance. The guidance uses patient-specific information to predict when adequate or desired images for detecting heart abnormality are acquired. The timing relative to recovery of the heart rate is used to guide the sonographer and/or assist in diagnosis.

The input 50 is an interface for electrical and physical connection with the ECG device 56. A cable from the ECG device 56 plugs into the input 50 for receiving electrode signals, a heart trace signal, and/or detected heart cycle information (e.g., R wave timing and/or interval). The plug-in is releasable so that the input 50 is connectable with the ECG device 56. The received ECG data is from a specific patient during the stress echocardiography, so is patient specific.

The processor 52 is a general processor, digital signal processor, controller, application specific integrated circuit, field programmable gate array, timer, analog circuit, digital circuit, combinations thereof, or other now known or later developed device for computing a time relative to heart rate recovery. The processor 52 receives the ECG data, calculates patient-specific characteristic of the recovery of the patient's heart rate from stress, and computes timing information relative to the recovery. For example, the processor 52 is configured by hardware, software, and/or firmware to calculate a post-stress time window for the stress echocardiography of the patient. The post-stress time window is a period during which the heart rate is still recovering. Abnormalities of the heart may be more easily detected in images during the recovery period as opposed to times when the heart rate is mostly or completely recovered from the stress. The processor 52 calculates the time window using the electrocardiography information received at the input 50. For example, the R-R interval based on ECG data or received at the input 50 is used to determine a value for a variable. The value is used in calculating the time window.

The processor 52 is configured to output to a speaker or the display 48. The time relative to the post-stress time window is output during the stress echocardiography. The time remaining before recovery and/or during which more diagnostically useful imaging occurs is indicated to the user visually or audibly. For example, the image processor 46 outputs an image or image sequence representing the heart of the patient. The processor 52 adds text, graph, or other indicator to or by the images of the heart. The text, graph, or other indicator shows the timing information. The display 48 is configured by the output from the processor 52 to indicate a time relative to the post-stress time window during the stress echocardiography. The output may be for review of previously acquired images in other embodiments.

The memory 54 is a non-transitory computer readable storage medium, such as a cache, buffer, RAM, removable media, hard drive or other computer readable storage media. Computer readable storage media include various types of volatile and nonvolatile storage media. The memory 54 stores ECG data, recovery information, recovery model, patient-specific information, images, indicators, or other information for guidance of stress echocardiography. Input, output, and/or information being processed is stored.

The memory 54 or another memory stores instructions for the processor 52 and/or other processors. Data representing instructions executable by a programmed processor for stress echocardiography guidance is stored in the memory. The instructions are for implementing the processes, methods and/or techniques discussed herein. The functions, acts or tasks illustrated in the figures or described herein are executed in response to one or more sets of instructions stored in or on the computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for stress echocardiography guidance, the method comprising:
   detecting, during stress echocardiography, a plurality of heart rate intervals of a patient from an EKG device;
   calculating, by an ultrasound imaging system, a rate of recovery for the patient from the heart rate intervals, the recovery being recovery from abnormal wall motion after cessation of stress;
   estimating, by the ultrasound imaging system, an amount of time for imaging a heart of the patient while recovering from stress, the amount of time estimated as a function of the rate of recovery; and
   outputting the amount of time on a display of the ultrasound imaging system.

2. The method of claim 1 wherein detecting comprises detecting RR intervals.

3. The method of claim 1 wherein detecting comprises detecting at least three heart rate intervals.

4. The method of claim 1 wherein detecting the heart rate intervals comprises detecting lengths of heart cycles.

5. The method of claim 1 wherein calculating comprises fitting an exponential curve to the heart rate intervals as a function of time.

6. The method of claim 1 wherein calculating comprises calculating a time constant for the patient, and wherein estimating comprises calculating a change in time of a heart rate as a function of the time constant, the amount of time being a current time plus the change.

7. The method of claim 1 wherein calculating the rate of recovery comprises performing a linear regression.

8. The method of claim 1 wherein estimating the time comprises estimating the amount of time as a function of a threshold.

9. The method of claim 8 wherein estimating the time as a function of the threshold comprises estimating as a function of a recovery rate threshold.

10. The method of claim 1 wherein estimating the amount of time comprises estimating the amount of time as a function of a heart rate derived from the rate of recovery, the rate of recovery comprising a change in the heart rate intervals as a function of time.

11. The method of claim 1 wherein outputting comprises outputting the amount time as text, a graph, or text and a graph.

12. The method of claim 1 wherein outputting comprises outputting the amount of time as associated with an image displayed during review.

13. The method of claim 1 further comprising:
   detecting other heart rate intervals;
   repeating the calculating, estimating, and outputting using the other heart rate intervals.

14. A non-transitory computer readable storage medium having stored therein data representing instructions executable by a programmed processor for stress echocardiography guidance, the storage medium comprising instructions for:
   computing a time for image acquisition during stress echocardiography of a patient with an ultrasound scanner, the time indicating a duration related to post-stress abnormal wall motion;
   adapting the computing as a function of an electrocardiography signal for the patient and from an electrocardiography sensor, the adapting resulting in the duration being specific to the patient; and
   outputting an indication of the time.

15. The non-transitory computer readable storage medium of claim 14, wherein computing comprises computing as a function of a heart rate of the patient and a time constant, and wherein adapting comprises calculating the time constant from a change in the heart rate as a function of time from the electrocardiography signal of the patient.

16. The non-transitory computer readable storage medium of claim 14, wherein computing comprises computing as a function of a threshold heart rate.

17. The non-transitory computer readable storage medium of claim 14, wherein adapting comprises adapting as a function of a curve representing recovery of a heart rate of the patient fit to information from the electrocardiography signal of the patient.

18. The non-transitory computer readable storage medium of claim 14, wherein outputting the indication comprises outputting a visual, auditory, or visual and auditory indication of the time relative to recovery of a heart rate of the patient.

19. A system for stress echocardiography guidance, the system comprising:
   an ultrasound scanner configured for performing stress echocardiography of a patient;
   an input of the ultrasound scanner connectable with an electrocardiography device; and
   a processor configured to calculate a post-stress time window for time remaining for performing the stress echocardiography of the patient, the post-stress time window calculated as a function of electrocardiography information received at the input.

20. The system of claim 19 further comprising an output configured to indicate the time during the stress echocardiography.

* * * * *